US00PP18887P2

(12) United States Plant Patent
van Kleinwee et al.

(10) Patent No.: US PP18,887 P2
(45) Date of Patent: Jun. 3, 2008

(54) ***BIDENS FERULIFOLIA* PLANT NAMED 'BIDOLBE'**

(50) Latin Name: *Bidens ferulifolia*
Varietal Denomination: Bidolbe

(75) Inventors: Theodorus Cornelis Maria van Kleinwee, Hoorn (NL); Anna M. W. P. Houbraken, Enkhuizen (NL)

(73) Assignee: Syngenta Seeds B. V., Enkhuizen (NL)

( * ) Notice: Subject to any disclaimer, the term of this patent is extended or adjusted under 35 U.S.C. 154(b) by 23 days.

(21) Appl. No.: 11/639,572

(22) Filed: Dec. 15, 2006

(51) Int. Cl.
*A01H 5/00* (2006.01)

(52) U.S. Cl. ..... Plt./263
(58) Field of Classification Search ..... Plt./263
See application file for complete search history.

*Primary Examiner*—Annette H Para
(74) *Attorney, Agent, or Firm*—S. Matthew Edwards

(57) ABSTRACT

A new *Bidens* plant named 'Bidolbe' particularly distinguished by its very compact plant habit, short internodes, golden yellow flowers, and hardly any seed set.

1 Drawing Sheet

Latin name of the genus and species of the plant claimed: *Bidens ferulifolia.*
Varietal denomination: 'Bidolbe'.

BACKGROUND OF THE NEW PLANT

The present invention relates to a new distinct cultivar of *Bidens,* botanically known as *Bidens ferulifolia,* native to South USA and Mexico.

The new cultivar is propagated by cuttings resulting from a seedling from *Bidens ferulifolia* cv. 'Bidtis 1' (U.S. Plant Pat. No. 12,280). Seed of 'Bidtis 1,' resulting from open pollination, was harvested in 2000 and the new variety 'Bidolbe' was selected in 2001 as one of the plants of this population. This new plant is an annual.

The new cultivar is a product of a planned breeding program conducted by the inventor in Enkhuizen, The Netherlands. The objective of the breeding program was to develop a compact *Bidens* variety without seed set. 'Bidolbe' was asexually reproduced by cuttings for 5 years now and trialled under different conditions in Europe on Syngenta trial ground properties. The new variety is stable and reproduces true to type in successive generations of asexual reproduction.

DESCRIPTION OF THE DRAWING

This new *Bidens* plant is illustrated by the accompanying photographic drawing which shows blooms, buds and foliage of the plant in full color, the color shown being as true as can be reasonably obtained by conventional photographic procedures.

DESCRIPTION OF THE NEW CULTIVAR

The following detailed descriptions set forth the distinctive characteristics of this new *Bidens* plant. The data which defines these characteristics were collected from asexual reproductions carried out in Enkhuizen, Netherlands. The plant history was taken on 30 week old plants, grown in the open field in Enkhuizen, The Netherlands with day temperatures ranging from 16-30 degrees Celsius, and night temperatures ranging from 10-16 degrees Celsius.

Color references are primarily to the R.H.S. Color Chart of The Royal Horticultural Society of London.

TABLE 1

COMPARISON BETWEEN THE NEW CULTIVAR 'BIDOLBE' AND 'BIDCOMTIS'

| | 'Bidcomtis' (U.S. Ser. No. 10/899,777) | 'Bidolbe' |
|---|---|---|
| Plant height | 32-38 cm | 25-29 cm |
| Plant width | up to 80 cm | 65-85 cm |
| Seed set | Present | Hardly any seed set |
| Internode length | 2-4 cm | 1.9-3.7 cm |

The plant:

*Classification.*—Botanical: *Bidens ferulifolia* cv. 'Bidolbe'.

Parentage:

*Female parent.*—*Bidens ferulifolia* cv. 'Bidtis 1,' (U.S. Plant Pat. No. 12,280).

*Male parent.*—Unknown seedling or variety of *Bidens ferulifolia.*

*Breeders code of new variety.*—'C1010-2'.

Propagation:

*Type cuttings.*—Terminal cuttings.

*Time to initiated roots.*—10-12 days at air temperature of 21° C.

*Time to develop roots.*—14-18 days at air temperature of 17° C.

Plant description:

*Growth habit.*—Ball to flat shaped, with trailing branches at the bottom of the plant. Good filled surface, flowering all over plant.

*Plant height.*—25-29 cm.

*Vigor.*—Somewhat less vigorous than *Bidens ferulifolia* cv. 'Bidcomtis'.

*Spreading area of plant.*—65-85 cm.

*Strength.*—Resistant to hot and cold weather.

*Branching character.*—Freely branching and lateral branching at every node.

*Number of branches per plant.*—8 branches/plant, near base of plant branching in many more branches.

*Crop time.*—12 weeks.

The stem:

*Diameter.*—Up to 5 mm in old stems, 1 mm in very young stems.

*Shape.*—Cylindrical.

*Length of plant stem.*—Up to 49 cm.

*Length of lateral branch.*—Up to 49 cm.

*Anthocyanin pigmentation.*—Present, can get as dark as RHS N199B in old stems.

*Length of internode.*—1.9-3.7 cm depending on light conditions.

*Pubescence.*—Present.

*Color.*—Young stem: RHS 144B. Older stem: Between 59A and N79B with anthocyan pigmentation RHS 200C.

The foliage:

*Arrangement.*—Opposite, but alternate on flower stems.

*Shape of leaf.*—2-pinnate fern-like leaves.

*Leaf apex.*—Apiculate.

*Leaf base.*—Acute.

*Leaf margin.*—Lancinate.

*Texture.*—Smooth young leaves.

*Leaf length.*—1.5-2.5 cm in old, flowering plants, up to 5.5 cm in young, vegetative plants.

*Leaf width.*—2-3 cm.

*Depth of incision.*—Fully incised.

*Color.*—Upper side: Young leaf RHS 143A. Old leaf RHS 137A, more anthocyan in very old leaf: RHS 147A. Lower side: Young leaf RHS 144A. Old leaf RHS 146B.

*Pubescence.*—Some pubescence near base of petiole. Absent in rest of leaf and petiole.

*Petiole.*—Length: 0.4-1.1 cm. Color: Lower side RHS 152A, upper side N199B. Diameter: 1 mm.

*Venation.*—Shape: Pinnate. Color: RHS 143B, upper and lower surface.

The bud:

*Peduncle.*—Length: 2.5-5.5 cm. Diameter: 1 mm. Angle: 45° at base of peduncle; bending more towards main stem at the end. Strength: Flexible. Color: Green, RHS 143A, occasionally some anthocyanin pigmentation; RHS 143B.

*Size of the bud.*—Length: 0.6-0.8 cm. Diameter: 0.4 cm.

*Shape.*—Oblong.

*Color.*—RHS 9A.

The inflorescence:

*Flowering season.*—Continuous and free flowering throughout spring, summer and fall.

*Diameter of disc.*—2.0-3.0 cm.

*Depth of disc.*—6 mm.

*Form.*—Capitulum with 1 series of ray florets and more series of disc florets.

*Overlapping of ray florets.*—Separate ray florets, but little overlap in flower head.

*Receptacle.*—Shape: Brush-shape. Height: 3 mm. Color: RHS 145B.

*Fragrance.*—Weak.

*Number of flowers per plant.*—±100 flowers per plant depending on growth conditions and age of plant.

*Lastingness of flowers on plant.*—7 days.

Ray florets:

*No. of ray florets per inflorescence.*—5, rarely 4 or 6.

*Size.*—Length: 0.9-1.3 cm. Width: 0.5-1 cm.

*Ray floret.*—Shape: Ovate. Apex: Tri-dentate. Base: Obtuse. Margin: Entire. Texture: Smooth.

*Color.*—Upper side: More bright and intense golden yellow than RHS 9A. Lower side: RHS 9A.

Disc florets:

*No. of disc florets per inflorescence.*—±45 disc florets/inflorescence.

*Size.*—Length: 4-6 mm. When in flower: 4-6 mm. Width: 0.5 mm.

*Disc floret.*—Shape: Tubular, elongated. Apex: Five-pointed. Base: Fused. Margin: Entire. Texture: Smooth.

*Color of upper and lower side.*—RHS 14A.

Phyllary:

*Number of phyllaries.*—7-8 green ones (RHS 139A) at the lower part of the receptacle and 6-7 yellow ones (RHS 9A) near to the ray florets.

*Size.*—Length: 2-3 mm. Width: 0.5 mm. Shape: Elongated elliptic. Apex: Acute. Base: Truncate. Margin: Entire. Texture: Smooth.

Reproductive organs:

*Androecium.*—Location: Present on disc florets only. Anther color: RHS 200A. Anther size: 1.3 mm long. Stamen number: 5. Pollen color: RHS 17A. Amount of pollen: Few.

*Gynoecium.*—Location: Present on ray and disc florets. Pistil number: ±45 pistils/inflorescence. Pistil length: 4 mm. Style length: 2 mm. Ovary Number: one per pistil. Size: 0.2 mm diameter, 1.1 mm long. Ovary color: RHS 149D. Style color: RHS 15A. Stigma shape: Bifurcate. Stigma color: RHS 15A.

Seed:

*Production.*—Very few.

*Size.*—Length: 0.6-0.7 cm, including awns of 0.9 mm. Diameter: 0.5 mm.

*Color.*—RHS N200A.

*Shape.*—2 rigid awns with minute reflexed points on the achene.

Disease resistance and tolerance for weather conditions: Good tolerance to heat. No specific susceptibility for pests or diseases has been observed.

What is claimed is:

1. A new and distinct variety of *Bidens* plant, substantially as herein illustrated and described.

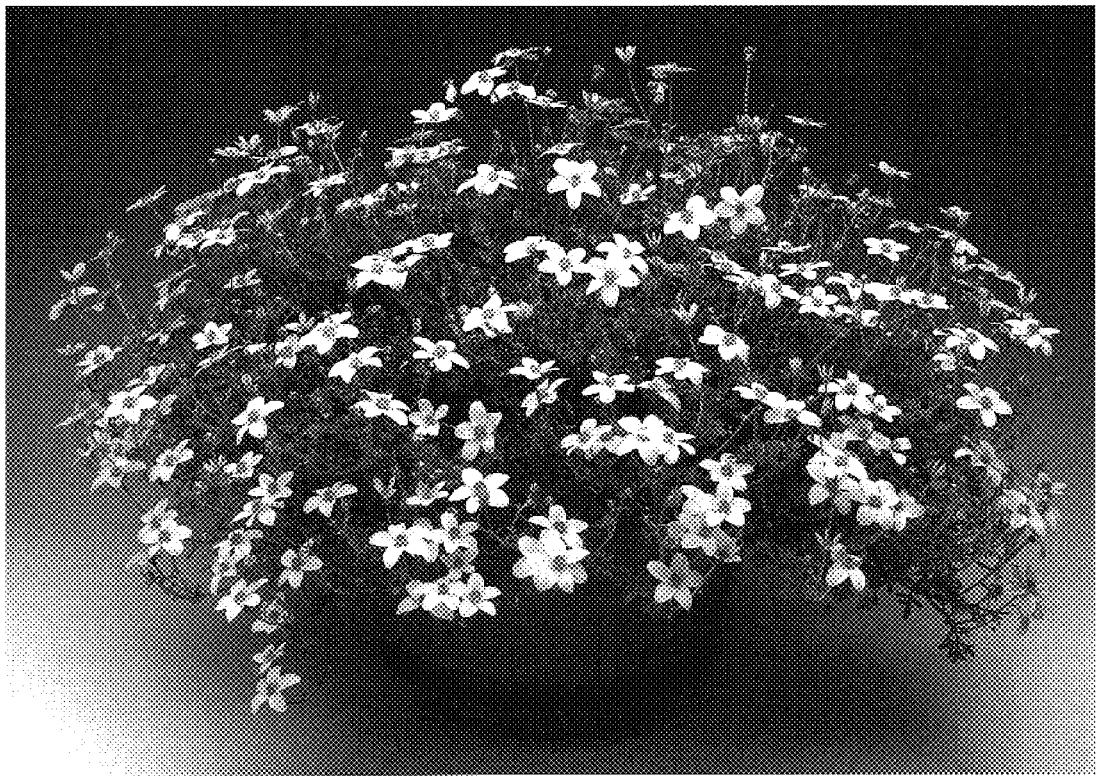

* * * * *